(12) United States Patent
Dyballa et al.

(10) Patent No.: US 9,879,353 B2
(45) Date of Patent: Jan. 30, 2018

(54) ELECTROCHEMICAL COUPLING OF TWO PHENOLS WHICH DIFFER IN THEIR OXIDATION POTENTIAL

(71) Applicants: Katrin Marie Dyballa, Recklinghausen (DE); Robert Franke, Marl (DE); Dirk Fridag, Haltern am See (DE); Siegfried R. Waldvogel, Gau-Algesheim (DE); Bernd Elsler, Bonn (DE)

(72) Inventors: Katrin Marie Dyballa, Recklinghausen (DE); Robert Franke, Marl (DE); Dirk Fridag, Haltern am See (DE); Siegfried R. Waldvogel, Gau-Algesheim (DE); Bernd Elsler, Bonn (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/772,874

(22) PCT Filed: Dec. 10, 2013

(86) PCT No.: PCT/EP2013/076078
§ 371 (c)(1),
(2) Date: Sep. 4, 2015

(87) PCT Pub. No.: WO2014/135236
PCT Pub. Date: Sep. 12, 2014

(65) Prior Publication Data
US 2016/0010225 A1 Jan. 14, 2016

(30) Foreign Application Priority Data

Mar. 7, 2013 (DE) .................... 10 2013 203 865

(51) Int. Cl.
| | | |
|---|---|---|
| *C25B 3/10* | (2006.01) | |
| *C07C 43/23* | (2006.01) | |
| *C25B 15/02* | (2006.01) | |
| *C25B 9/08* | (2006.01) | |

(52) U.S. Cl.
CPC ............ *C25B 3/10* (2013.01); *C07C 43/23* (2013.01); *C25B 9/08* (2013.01); *C25B 15/02* (2013.01)

(58) Field of Classification Search
CPC .. C07C 43/23; C25B 9/08; C25B 3/10; C25B 15/02
See application file for complete search history.

(56) References Cited

U.S. PATENT DOCUMENTS 8,747,646 B2   6/2014   Fischer et al.

FOREIGN PATENT DOCUMENTS

| JP | 5-32579 | 2/1993 |
| JP | 2012528938 | 11/2012 |
| WO | WO 2010/139685 A1 | 12/2010 |
| WO | WO 2014/135237 A1 | 9/2014 |
| WO | WO 2014/135371 A1 | 9/2014 |
| WO | WO 2014/135405 A1 | 9/2014 |

OTHER PUBLICATIONS

Lin et al. ("Anti-inflammatory Biphenyls and Dibenzofurans form Rhaphioliepis indica", J. Nat. Prod., Sep. 2010, vol. 73, No. 10, pp. 1628-1631).*
Du et al. ("Diarylcyclopendione Metabolite Obtained from a Preussia typharum Isolated Using an Unconventional Cultivation Approach", Journal of Natural Products, Oct. 2012, 75 (10), pp. 1819-1823).*
Malkowsky et al. ("Unexpected Highly Chemoselective Anodic ortho-Coupling Reaction of 2,4-Dimethylphenol on Boron-Doped Diamond Electrodes", Eur. J. Org. Chem., Issue 20, Oct. 2006, pp. 4569-4572).*
Sartori et al. (J. Org. Chem., vol. 58, Issue 25, Dec. 1993, pp. 7271-7273).*
U.S. Appl. No. 14/773,228, filed Sep. 4, 2015, Dyballa, et al.
U.S. Appl. No. 14/773,224, filed Sep. 4, 2015, Dyballa, et al.
U.S. Appl. No. 14/773,102, filed Sep. 4, 2015, Dyballa, et al.
International Search Report dated Apr. 11, 2014 in corresponding PCT/EP2013/076078 filed Dec. 10, 2013 (with English translation of category of cited documents).
Milan Remko, "MO Investigations on Lignin Model Compounds", Zeitschrift Für Physikalische Chemie Neue Folge, Bd. 120, 1980, XP8167180, pp. 1-8.
Lin Du, et al., "Diarylcyclopentendione Metabolite Obtained from a Preussia typharum Isolate Procured Using an Unconventional Cultivation Approach", Journal of Natural Products, Bd. 75, Nr. 10, 2012, XP-002722560, pp. 1819-1823.
José C. del Río, et al., "Structural Characterization of Guaiacyl-rich Lignins in Flax(*Linum usitatissirpum*) Fibers and Shives", Journal of Agricultural and Food Chemistry, 2011, 59, XP-002722561, pp. 11088-11099.
Axel Kirste, et al., "Anodic Phenol-Arene Cross-Coupling Reaction on Boron-Doped Diamond Electrodes", Angewandte Chemie, 2010, 49, XP-002595230, pp. 971-975.
Office Action dated Apr. 8, 2016 in German Patent Application No. 10 2013 203 865.8.
Axel Kirste, et al., "Efficient Anodic and Direct Phenol-Arene C,C Cross-Coupling: The Benign Role of Water or Methanol" Journal of the American Chemical Society, vol. 134, 2012, pp. 3571-3576.
Written Opinion dated Jun. 20, 2016 in Singaporean Patent Application No. 11201507160S.
Office Action dated Oct. 18, 2016 in Taiwanese Patent Application No. 103107244 (with English Translation).
1402075-15-3 Registry as cited in JP Office Action dated Oct. 17, 2016, issued in corresponding application No. JP2015-560568.
Office Action issued Mar. 29, 2017 in Korean Patent Application No. 10 2015 7027237 (with English-language Translation).

* cited by examiner

*Primary Examiner* — Rosalynd A Keys
(74) *Attorney, Agent, or Firm* — Oblon, McClelland, Maier & Neustadt, L.L.P.

(57) ABSTRACT

Electrochemical process for coupling two phenols of different oxidation potential, and novel biphenols which can be prepared by this electrochemical coupling.

8 Claims, 4 Drawing Sheets

Figure 1:
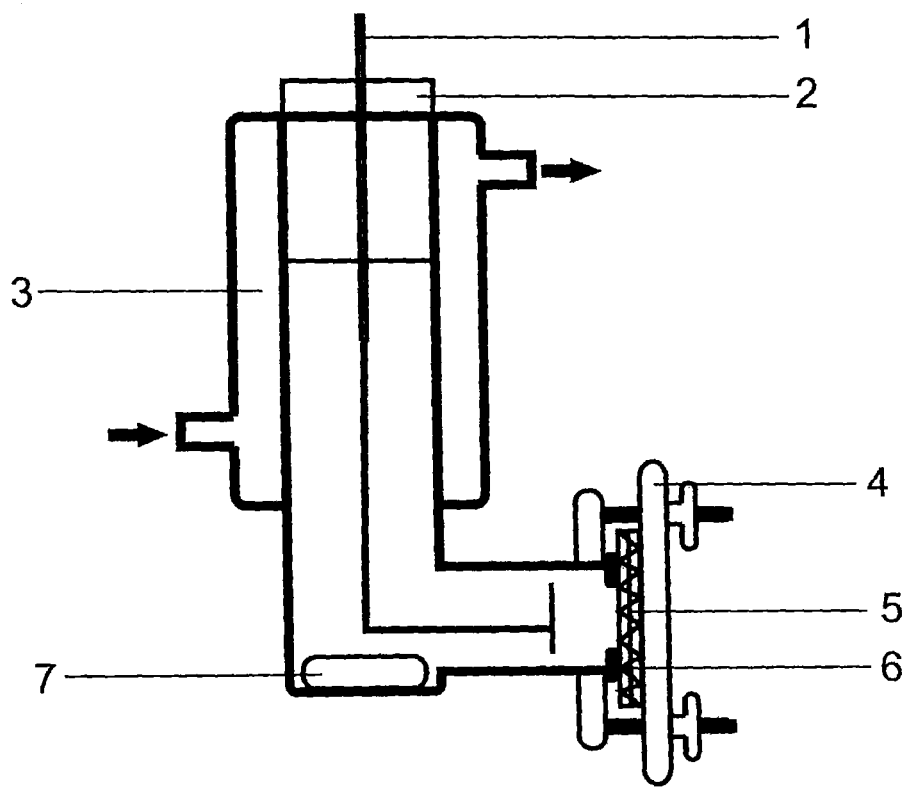

ELECTROCHEMICAL COUPLING OF TWO PHENOLS WHICH DIFFER IN THEIR OXIDATION POTENTIAL

The invention which follows relates to an electrochemical process for coupling two phenols of different oxidation potential. The invention further relates to novel biphenols which can be prepared, for example, by electrochemical coupling.

The term "phenols" is used as a generic term in this application and therefore also encompasses substituted phenols. Two phenols having a different oxidation potential must therefore also have different substitution.

Direct coupling of two different phenols has to date been described only by an electrochemical route: Sartori et al. J. Org. Chem. 1993, 58, 7271-7273. The coupling is effected here using an oxidizing agent such as $FeCl_3$, $VOCl_3$, p-benzoquinone, $CuBr_2$ or 2,3-dichloro-5,6-dicyano-1,4-benzoquinone (DDQ), and with addition of $AlCl_3$.

Disadvantages of the methods described by Sartori et al. are need for the dry solvents and for exclusion of air. Furthermore, large amounts of oxidizing agents, some of which are toxic (e.g. DDQ), are used. During the reaction, toxic by-products occur, which have to be separated in a complex manner from the desired product and disposed of in an expensive manner.

To date, the coupling only of identical phenols by an electrochemical route has been successfully conducted and described: Kirste et al. Chem. Eur. J. 2011, 17, 14164-14169; Kirste et al. Org. Lett., Vol. 13, No. 12, 2011; Kirste et al. Chem. Eur. J. 2009, 15, 2273-2277.

A problem which occurs in the electrochemical coupling of different molecules is that the co-reactants generally have different oxidation potentials $E_{Ox}$. The result of this is that the molecule having the lower oxidation potential has a higher propensity to release an electron (e⁻) to the anode and an H⁺ ion to, for example, the solvent than the molecule having the higher oxidation potential. The oxidation potential $E_{Ox}$ can be calculated via the Nernst equation:

$$E_{Ox} = E° + (0.059/n) * lg([Ox]/[Red])$$

$E_{Ox}$: electrode potential for the oxidation reaction (=oxidation potential)
E°: standard electrode potential
n: number of electrons transferred
[Ox]: concentration of the oxidized form
[Red]: concentration of the reduced form If the processes cited in the literature above were to be applied to two different phenols, the result of this would be to form predominantly free radicals of the molecule having a lower oxidation potential, which would then react with themselves. By far the predominant main product obtained would thus be a biphenol which has formed from two identical phenols. This problem does not occur in the coupling of identical molecules.

The problem addressed by the invention which follows was to provide an electrochemical process in which phenols having different oxidation potentials can be coupled to one another, and the yield of the biphenol formed from two different phenols is above that as achievable by the electrochemical methods known from the literature, i.e. above that of the biphenol formed from two different phenols.

In addition, novel biphenols were to be synthesized.

The problem is solved by a process according to Claim 8.

Compound of one of the general formulae (I) to (III):

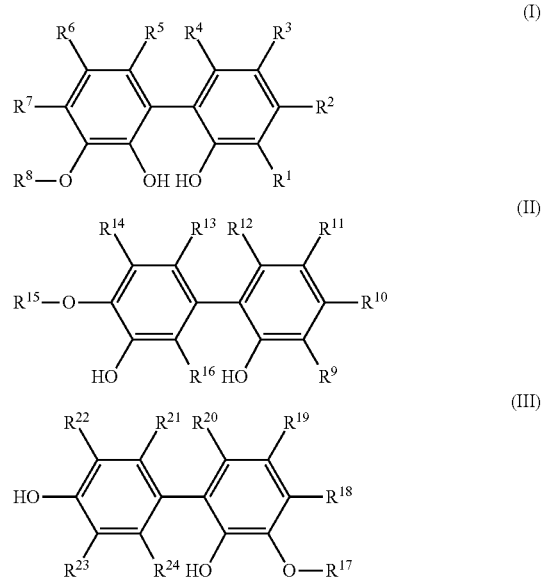

where $R^2$, $R^3$, $R^4$, $R^5$, $R^6$, $R^7$, $R^{10}$, $R^{11}$, $R^{12}$, $R^{13}$, $R^{14}$, $R^{16}$, $R^{18}$, $R^{19}$, $R^{20}$, $R^{21}$, $R^{24}$ are selected from:
—H, -alkyl, —O-alkyl, —O-aryl, —S-alkyl, —S-aryl;
$R^8$, $R^{15}$, $R^{17}$ are -alkyl;
$R^1$, $R^9$, $R^{22}$, $R^{23}$ are selected from: —H, -alkyl;
and, if $R^3$ is -Me, $R^1$ and $R^2$ are not both —H.

Alkyl is an unbranched or branched aliphatic carbon chain having 1 to 10 carbon atoms. The carbon chain preferably has 1 to 6 carbon atoms, more preferably 1 to 4 carbon atoms.

Aryl for aromatic (hydrocarbyl) radicals, preferably having up to 14 carbon atoms, e.g. phenyl-($C_6H_5$—), naphthyl-($C_{10}H_7$—), anthryl- ($C_{14}H_9$—), preferably phenyl.

In one embodiment of the invention, $R^2$, $R^3$, $R^4$, $R^5$, $R^6$, $R^7$, $R^{10}$, $R^{11}$, $R^{12}$, $R^{13}$, $R^{14}$, $R^{16}$, $R^{18}$, $R^{19}$, $R^{20}$, $R^{21}$, $R^{24}$ are selected from: —H, -alkyl, —O-alkyl, —O-aryl.

In one embodiment of the invention, $R^2$, $R^3$, $R^4$, $R^5$, $R^6$, $R^7$, $R^{10}$, $R^{11}$, $R^{12}$, $R^{13}$, $R^{14}$, $R^{16}$, $R^{18}$, $R^{19}$, $R^{20}$, $R^{21}$, $R^{24}$ are selected from: —H, -alkyl.

In one embodiment of the invention, $R^4$ and $R^5$ are —H.
In one embodiment of the invention, $R^3$ and $R^6$ are -alkyl.
In one embodiment of the invention, $R^1$ is —O-alkyl.
In one embodiment of the invention, $R^{13}$ is -alkyl.
In one embodiment of the invention, $R^{19}$ is -alkyl.

As well as the compounds, also claimed is a process by which, for example, the abovementioned compounds can be prepared.

Electrochemical process for preparing biphenols, comprising the process steps of:
a) introducing a solvent or solvent mixture and a conductive salt into a reaction vessel,
b) adding a first phenol having an oxidation potential $|E_{Ox}1|$ to the reaction vessel,
c) adding a second phenol having an oxidation potential $|E_{Ox}2|$ to the reaction vessel, where:

$$|E_{Ox}2| > |E_{Ox}1| \text{ and } |E_{Ox}2| - |E_{Ox}1| = |\Delta E|,$$

the second phenol being added in excess relative to the first phenol,
and the solvent or solvent mixture being selected such that $\Delta E$ is in the range from 10 mV to 450 mV,
d) introducing two electrodes into the reaction solution,
e) applying a voltage to the electrodes, f) coupling the first phenol to the second phenol to give a biphenol.

Process steps a) to d) can be effected here in any sequence.

One aspect of the invention is that the yield of the reaction can be controlled via the difference in the oxidation potentials ($|\Delta E|$) of the two phenols.

The process according to the invention solves the problem mentioned at the start.

For efficient conduct of the reaction, two reaction conditions are necessary:
the phenol having the higher oxidation potential (second phenol) has to be added in excess, and
the difference in the two oxidation potentials ($|\Delta E|$) has to be within a particular range.

If the first condition is not met, the main product formed is the biphenol which forms through the coupling of two molecules of the first phenol.

If $|\Delta E|$ is too small, too much biphenol which forms through the coupling of two molecules of the second phenol is by-produced.

If, in contrast, $|\Delta E|$ is too large, an excessively high excess of the second phenol would be required, which would make the reaction uneconomic.

For the process according to the invention, knowledge of the absolute oxidation potentials of the two phenols is not absolutely necessary. It is sufficient when the difference in the two oxidation potentials from one another is known.

A further aspect of the invention is that the difference in the two oxidation potentials ($|\Delta E|$) can be influenced via the solvents or solvent mixtures used.

For instance, the difference in the two oxidation potentials ($|\Delta E|$) can be moved into the desired range by suitable selection of the solvent/solvent mixture.

Proceeding from 1,1,1,3,3,3-hexafluoroisopropanol (HFIP) as the base solvent, a $|\Delta E|$ which is too small can be increased, for example, by addition of alcohol. A $|\Delta E|$ which is too large can be lowered, in contrast, by addition of water.

The reaction sequence which proceeds is shown in the following scheme:

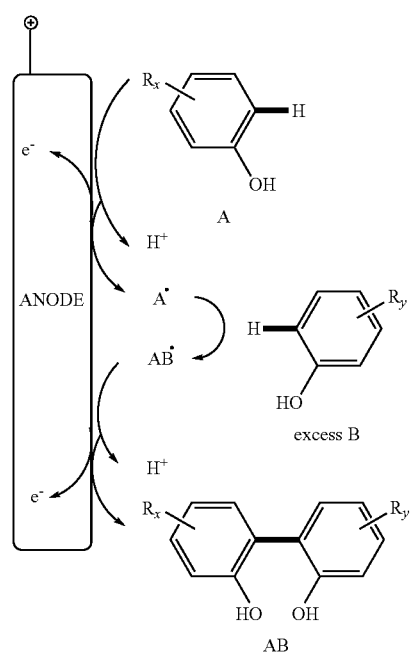

First of all, the compound A having the lower oxidation potential releases an electron to the anode. Because of the positive charge, the compound A becomes a very strong acid and spontaneously releases a proton. The radical thus formed then reacts with the compound B which is present in the solution in excess relative to the compound A. The biphenol AB radical formed by the coupling releases an electron to the anode and a proton to the solvent.

If the phenol B had not been added in excess, the phenol A radical would react with a second phenol A radical to give the corresponding biphenol AA.

With the aid of the process according to the invention, it has been possible for the first time to electrochemically couple phenols having different oxidation potentials in good yields.

In one variant of the process, the conductive salt is selected from the group of alkali metal, alkaline earth metal, tetra($C_1$-$C_6$-alkyl)ammonium, 1,3-di($C_1$-$C_6$-alkyl)imidazolium and tetra($C_1$-$C_6$-alkyl)phosphonium salts.

In one variant of the process, the counter ions of the conductive salts are selected from the group of sulphate, hydrogensulphate, alkylsulphates, arylsulphates, alkylsulphonates, arylsulphonates, halides, phosphates, carbonates, alkylphosphates, alkylcarbonates, nitrate, tetrafluoroborate, hexafluorophosphate, hexafluorosilicate, fluoride and perchlorate.

In one variant of the process, the conductive salt is selected from tetra($C_1$-$C_6$-alkyl)ammonium salts, and the counterion is selected from sulphate, alkylsulphate, arylsulphate.

In one variant of the process, the second phenol is used at least in twice the amount relative to the first phenol.

In one variant of the process, the ratio of the first phenol to the second phenol is in the range from 1:2 to 1:4.

In one variant of the process, either the first phenol the second phenol has an —O-alkyl group.

In one variant of the process, the solvent or solvent mixture is selected such that $|\Delta E|$ is in the range from 20 mV to 400 mV, preferably in the range from 30 mV to 350 mV.

In one variant of the process, the reaction solution is free of fluorinated compounds.

In one variant of the process, the reaction is free of transition metals.

In one variant of the process, the reaction solution is free of substrates having departing functionalities other than hydrogen atoms.

In the process claimed, it is possible to dispense with leaving groups at the coupling sites apart from hydrogen atoms.

In one variant of the process, the reaction solution is free of organic oxidizing agents.

In one variant of the process, the first phenol and the second phenol are selected from: Ia, Ib, IIa, IIb, IIIa, IIIb:

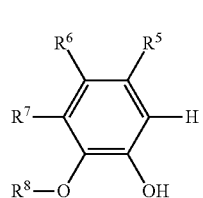

(Ia)

-continued

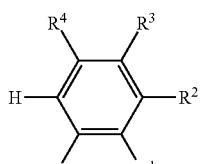
(Ib)

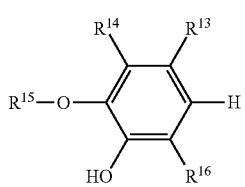
(IIa)

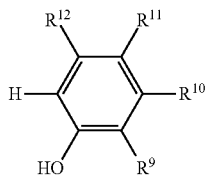
(IIb)

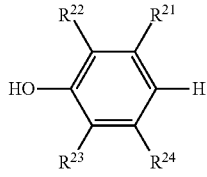
(IIIa)

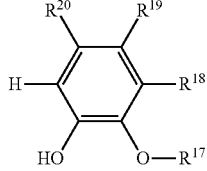
(IIIb)

where $R^2$, $R^3$, $R^4$, $R^5$, $R^6$, $R^7$, $R^{10}$, $R^{11}$, $R^{12}$, $R^{13}$, $R^{14}$, $R^{16}$, $R^{18}$, $R^{19}$, $R^{20}$, $R^{21}$, $R^{24}$ are selected from:
—H, -alkyl, —O-alkyl;
$R^8$, $R^{15}$, $R^{17}$ are -alkyl;
$R^1$, $R^9$, $R^{22}$, $R^{23}$ are selected from: —H, -alkyl,
and the following combinations are possible here:

| first phenol  | Ia | Ib | IIa | IIb | IIIa | IIIb |
| --- | --- | --- | --- | --- | --- | --- |
| second phenol | Ib | Ia | IIb | IIa | IIIa | IIIa |

Alkyl is an unbranched or branched aliphatic carbon chain having 1 to 10 carbon atoms. The carbon chain preferably has 1 to 6 carbon atoms, more preferably 1 to 4 carbon atoms.

Aryl for aromatic (hydrocarbyl) radicals, preferably having up to 14 carbon atoms, e.g. phenyl-($C_6H_5$—), naphthyl-($C_{10}H_7$—), anthryl- ($C_{14}H_9$—), preferably phenyl.

In one variant of the process, if $R^3$ is -Me, $R^1$ and $R^2$ are not both —H.

The invention is illustrated in detail hereinafter by working examples and a figure.

FIG. 1 shows a reaction apparatus in which the above-described coupling reaction can be performed. The apparatus comprises a nickel cathode (1) and an anode composed of boron-doped diamond (BDD) on silicon (5). The apparatus can be cooled with the aid of the cooling jacket (3). The arrows here indicate the flow direction of the cooling water. The reaction space is closed by a Teflon stopper (2). The reaction mixture is mixed by a magnetic stirrer bar (7). On the anode side, the apparatus is closed by screw clamps (4) and seals (6).

Figure 2:
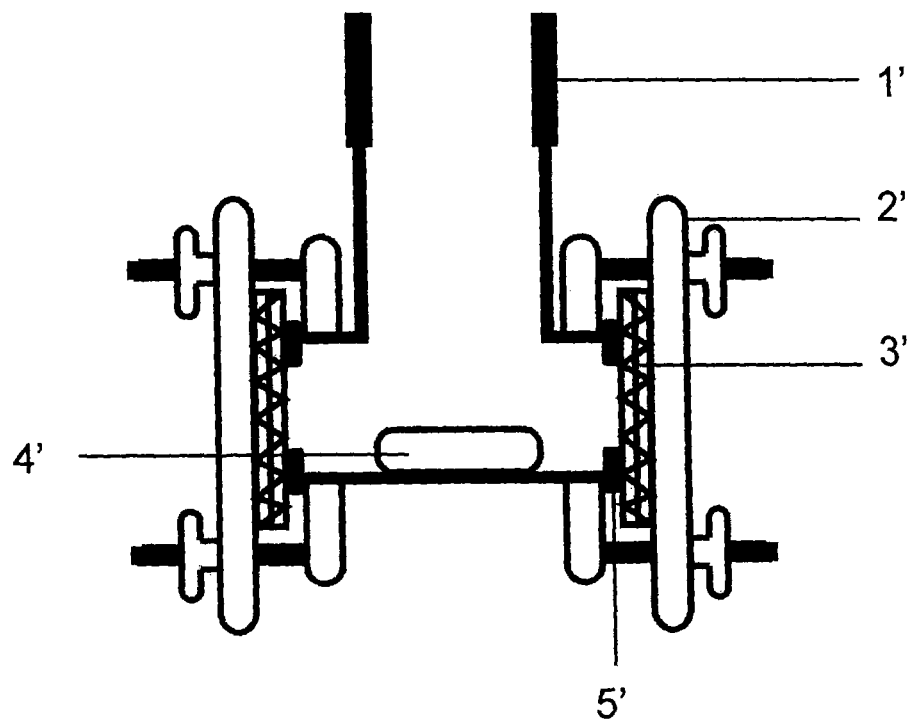

FIG. 2 shows a reaction apparatus in which the above-described coupling reaction can be performed on a larger scale. The apparatus comprises two glass flanges (5'), which are used to apply pressure, through screw clamps (2') and seals, to electrodes (3') composed of carrier materials coated with boron-doped diamond (BDD), or other electrode materials known to those skilled in the art. The reaction space may be provided with a reflux condenser via a glass sleeve (1'). The reaction mixture is mixed with the aid of a magnetic stirrer bar (4').

Figure 3:
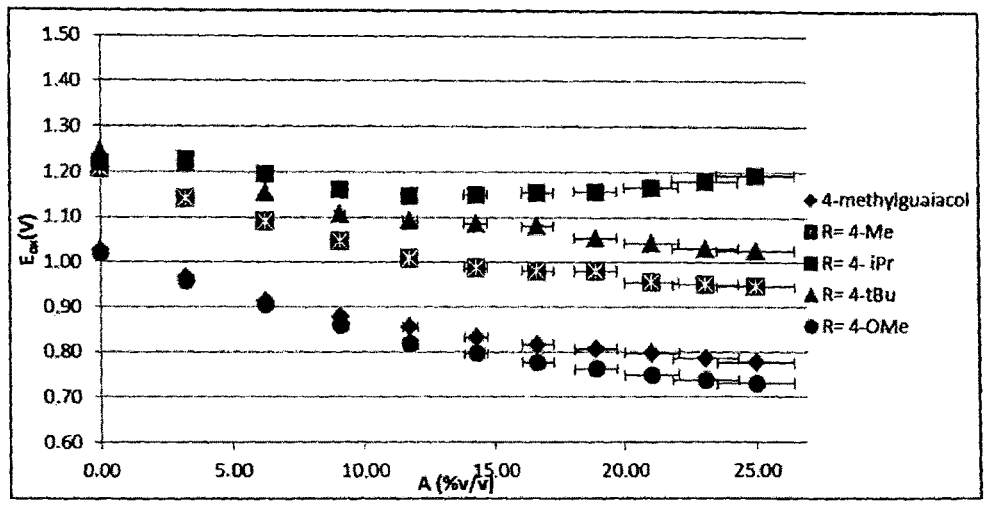

In FIG. 3, the dependence of the oxidation potential $\Delta E_{Ox}$ of the para substituents on the amount of methanol added is plotted.

Figure 4:
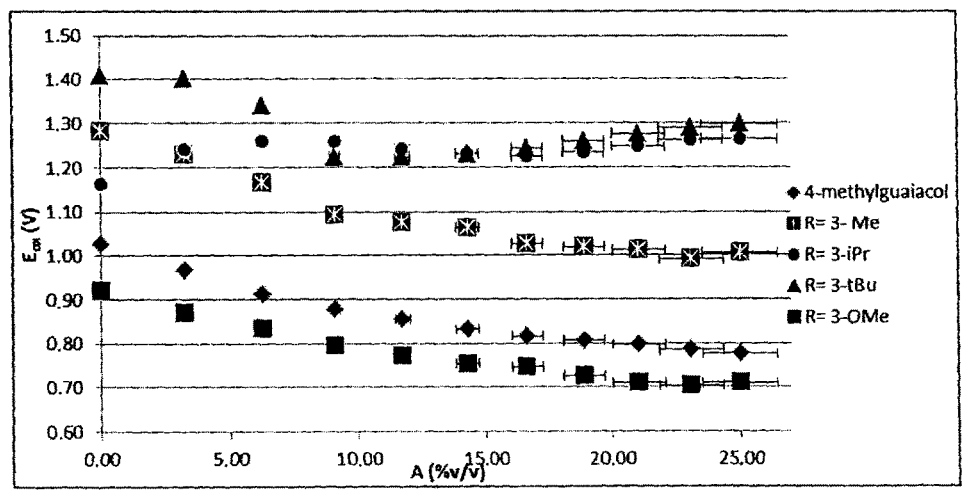

In FIG. 4, the dependence of the oxidation potential $\Delta E_{Ox}$ of the meta substituents on the amount of methanol added is plotted.

Figure 5:
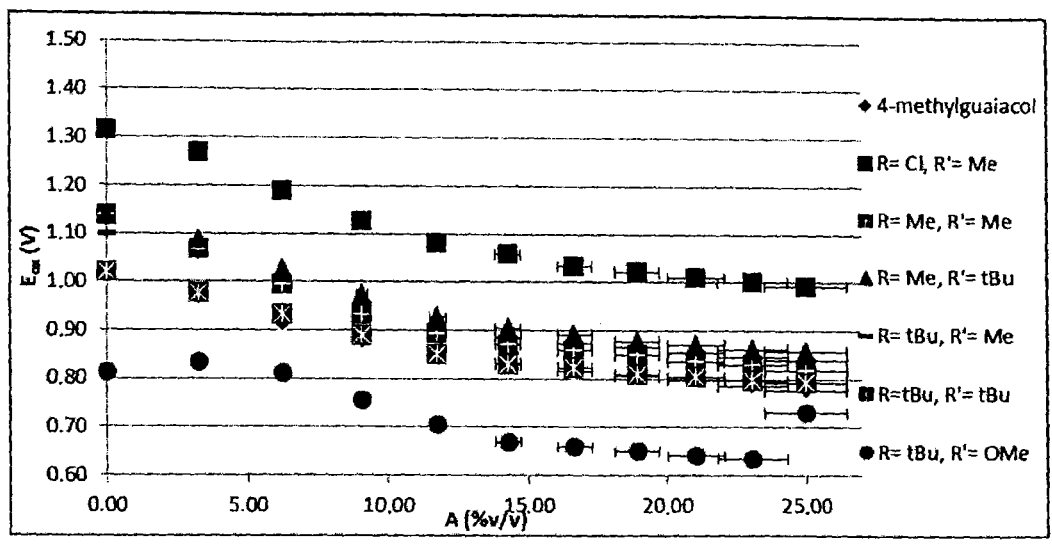

In FIG. 5, the dependence of the oxidation potential $\Delta E_{Ox}$ of the 2,4-disubstituted phenols on the amount of methanol added is plotted.

Figure 6:
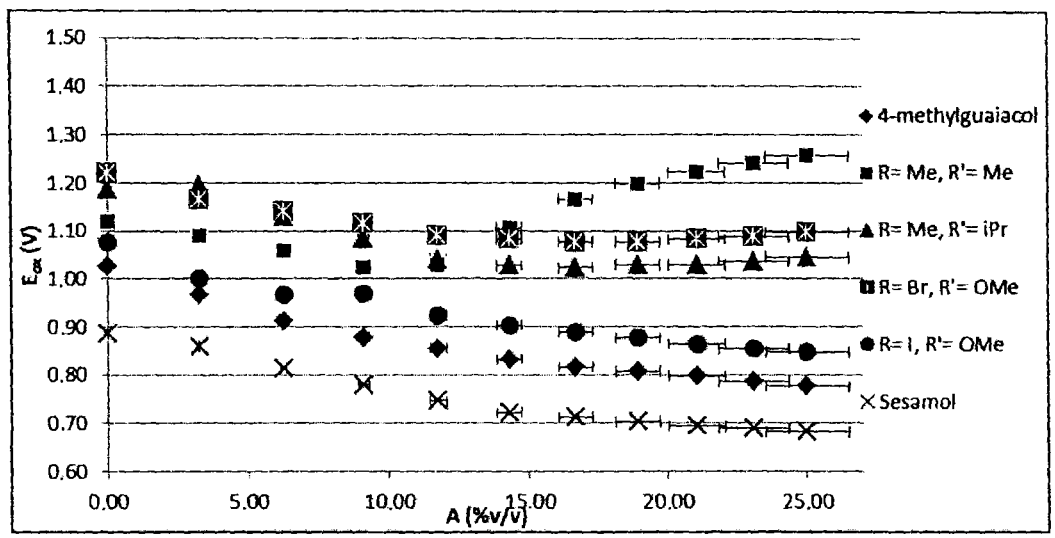

In FIG. 6, the dependence of the oxidation potential $\Delta E_{Ox}$ of the 3,4-disubstituted phenols on the amount of methanol added is plotted.

Analysis

Chromatography

The preparative liquid chromatography separations via "flash chromatography" were conducted with a maximum pressure of 1.6 bar on 60 M silica gel (0.040-0.063 mm) from Macherey-Nagel GmbH & Co, Düren. The unpressurized separations were conducted on Geduran Si 60 silica gel (0.063-0.200 mm) from Merck KGaA, Darmstadt. The solvents used as eluents (ethyl acetate (technical grade), cyclohexane (technical grade)) were purified beforehand by distillation on a rotary evaporator.

For thin-layer chromatography (TLC), ready-to-use PSC plates, silica gel 60 F254 from Merck KGaA, Darmstadt, were used. The Rf values are reported according to the eluent mixture used. The TLC plates were stained using a cerium-molybdatophosphoric acid solution as a dipping reagent: 5.6 g of molybdatophosphoric acid, 2.2 g of cerium (IV) sulphate tetrahydrate and 13.3 g of concentrated sulphuric acid in 200 ml of water.

Gas Chromatography (GC/GCMS)

The gas chromatography analyses (GC) of product mixtures and pure substances were effected with the aid of the GC-2010 gas chromatograph from Shimadzu, Japan. Measurement is effected on an HP-5 quartz capillary column from Agilent Technologies, USA (length: 30 m; internal diameter: 0.25 mm; film thickness of the covalently bound stationary phase: 0.25 μm; carrier gas: hydrogen; injector temperature: 250° C.; detector temperature: 310° C.; programme: "hard" method: start temperature 50° C. for 1 min, heating rate: 15° C./min, final temperature 290° C. for 8 min). Gas chromatography mass spectra (GCMS) of product mixtures and pure substances were recorded with the aid of the GC-2010 gas chromatograph combined with the GCMS-QP2010 mass detector from Shimadzu, Japan. Measurement is effected on an HP-1 quartz capillary column from Agilent Technologies, USA (length: 30 m; internal diameter: 0.25 mm; film thickness of the covalently bound stationary phase: 0.25 μm; carrier gas: hydrogen; injector temperature: 250° C.; detector temperature: 310° C.; programme: "hard" method: start temperature 50° C. for 1 min, heating rate: 15°

C./min, final temperature 290° C. for 8 min; GCMS: ion source temperature: 200° C.).

Melting Points

Melting points were measured with the aid of the SG 2000 melting point measuring instrument from HW5, Mainz and are uncorrected.

Elemental Analysis

The elemental analyses were conducted in the Analytical Division of the Department of Organic Chemistry at the Johannes Gutenberg University of Mainz on a Vario EL Cube from Foss-Heraeus, Hanau.

Mass Spectrometry

All electrospray ionization analyses (ESI+) were conducted on a QT of Ultima 3 from Waters Micromasses, Milford, Massachussetts. EI mass spectra and the high-resolution EI spectra were measured on an instrument of the MAT 95 XL sector-field instrument type from ThermoFinnigan, Bremen.

NMR Spectroscopy

The NMR spectroscopy studies were conducted on multinuclear resonance spectrometers of the AC 300 or AV II 400 type from Bruker, Analytische Messtechnik, Karlsruhe. The solvent used was $CDCl_3$. The $^1H$ and $^{13}C$ spectra were calibrated according to the residual content of undeuterated solvent according to the NMR Solvent Data Chart from Cambridge Isotopes Laboratories, USA. Some of the $^1H$ and $^{13}C$ signals were assigned with the aid of H,H COSY, H,H NOESY, H,C HSQC and H,C HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported with the number of bonds covered in Hertz (Hz). The numbers reported in the signal assignment correspond to the numbering given in the formula schemes, which need not correspond to IUPAC nomenclature.

General Procedure

The coupling reaction was conducted in an apparatus as shown in FIG. 1.

5 mmol of the first phenol having an oxidation potential $E_{Ox}1$ are dissolved together with 15 mmol of the second phenol having an oxidation potential $E_{Ox}2$ in the amounts specified in Table 1 below in 1,1,1,3,3,3-hexafluoroisopropanol (HFIP) and MeOH or in formic acid and MeOH. The electrolysis is effected under galvanostatic conditions. The outer jacket of the electrolysis cell is kept at a temperature of about 10° C. by means of a thermostat, while the reaction mixture is stirred and heated to 50° C. with the aid of a sand bath. After the end of the electrolysis, the cell contents are transferred with toluene into a 50 ml round-bottom flask and the solvent is removed under reduced pressure on a rotary evaporator at 50° C., 200-70 mbar. Unconverted reactant is recovered by means of short-path distillation (100° C., $10^{-3}$ mbar).

Electrode Material

Anode: boron-doped diamond (BDD) on Si

Cathode: Ni mesh

Electrolysis Conditions:

Temperature [T]: 50° C.

Current [I]: 15 mA

Current density [j]: 2.8 $mA/cm^2$

Quantity of charge [Q]: 2 F/mol of deficiency component

Terminal voltage [$U_{max}$]: 3-5 V

Syntheses

The synthesis of the biphenols was effected according to the above-described general procedure, and in a reaction apparatus as shown in FIG. 1.

2,2'-Dihydroxy-4',5-dimethyl-5'-(methylethyl)-3-methoxybiphenyl

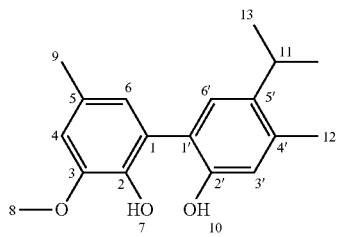

0.69 g (5 mmol, 1.0 equiv.) of 4-methylguaiacol and 2.28 g (15 mmol, 3.0 equiv.) of 3-methyl-4-(methylethyl)phenol were dissolved in 33 ml of HFIP, 0.68 g of MTES was added and the electrolyte was transferred into the electrolysis cell. The solvent and unconverted amounts of reactant are removed under reduced pressure after the electrolysis, the crude product is purified by flash chromatography on silica gel 60 in a 9:1 eluent (cyclohexane:ethyl acetate) and the product is obtained as a colourless solid.

Yield: 716 mg (50%, 2.5 mmol)
GC (hard method, HP-5): $t_R$=14.87 min
$R_f$(CH:EA=4:1)=0.43
$m_p$=126.8° C. (recrystallized from CH)
$^1H$ NMR (600 MHz, DMSO) δ=1.17-1.12 (m, 6H, 13-H), 2.24 (m, 6H, 9-H/12-H), 3.01 (dt, 1H, 11-H), 3.79 (s, 3H, 8-H), 6.55 (s, 1H, 6-H), 6.66 (d, 1H, 6'-H), 6.73 (d, 1H, 4-H), 6.96 (s, 1H, 3'-H), 8.16 (s, 1H, 7-H), 8.84 (s, 1H, 10-H);
Couplings: $^4J_{4-H,6-H}$=2.2 Hz, $^4J_{6-H,11-H}$=2.9 Hz, $^3J_{11-H,13-H}$=6.8 Hz;
$^{13}C$ NMR (151 MHz, DMSO) δ=18.73, 20.80 (C-9/C-12), 23.54 (C-13), 28.10 (C-11), 55.78 (C-8), 111.23 (C-4), 117.34 (C-6'), 123.42 (C-1'), 123.49 (C-6), 126.43 (C-1), 127.36 (C-5), 127.49 (C-3'), 134.40 (C-5'), 136.62 (C-4'), 141.12 (C-2), 147.65 (C-3), 151.69 (C-2').
HRMS for $C_{18}H_{22}O_3$ (ESI+) [M+Na$^+$]: calc.: 309.1467. found: 309.1457.
MS (EI, GCMS): m/z (%): 286 (50) [M]$^+$, 271 (100) [M–CH$_3$]$^+$, 244 (22) [M–C$_3$H$_6$]$^+$.
Elemental analysis for $C_{18}H_{22}O_3$: calc.: C, 75.50%; H, 7.74%. found: C, 75.01%; H, 7.70%.

2,2'-Dihydroxy-5,5'-dimethyl-3-methoxybiphenyl

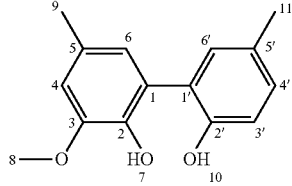

1.66 g (12 mmol, 1.0 equiv.) of 4-methylguaiacol and 3.91 g (36 mmol, 3.0 equiv.) of 4-methylphenol were dissolved in 65 ml of HFIP and 14 ml of MeOH, 1.63 g of MTES were added and the electrolyte was transferred to the electrolysis cell. The solvent and unconverted amounts of reactant are removed under reduced pressure after the electrolysis, the crude product is purified by flash chromatography on silica gel 60 in a 4:1 eluent (cyclohexane:ethyl acetate) and the product is obtained as a colourless solid.

Yield: 440 mg (36%, 1.8 mmol)
GC (hard method, HP-5): $t_R$=13.56 min
$R_f$(CH:EA=4:1)=0.38
$m_p$=162.0° C. (recrystallized from CH)
$^1$H NMR (400 MHz, DMSO) δ=2.18 (s, 3H, 9-H/11-H), 2.21 (s, 3H, 9-H/11-H), 3.76 (s, 3H, 8-H), 6.53 (s, 1H, 6-H), 6.71 (s, 1H, 4-H), 6.75 (d, 1H, 3'-H), 6.86-6.94 (m, 2H, 4'-H/6'-H), 8.53 (bs, 1H, 7-H/12-H);
Couplings: $^3J_{3'-H,4'-H}$=8.4 Hz;
$^{13}$C NMR (101 MHz, DMSO) δ=20.21, 20.77 (C-9/C-11), 55.79 (C-8), 111.36 (C-4), 115.69 (C-3'), 123.50 (C-6), 125.72 (C-1'), 126.16 (C-1), 127.20 (C-5), 127.30 (C-5'), 128.50 (C-6'), 131.83 (C-4'), 141.20 (C-2), 147.61 (C-3), 152.11 (C-2').

HRMS for $C_{15}H_{16}O_3$ (ESI+) [M+Na]$^+$: calc.: 267.0997. found: 267.0999.
MS (EI, GCMS): m/z (%): 244 (100) [M]$^+$, 229 (64) [M−CH$_3$]$^+$.
Elemental analysis for $C_{15}H_{16}O_3$: calc.: C, 73.75%; H, 6.60%. found: C, 73.81%; H, 6.54%.

2,5'-Dihydroxy-4',5-dimethoxy-2'-methylbiphenyl

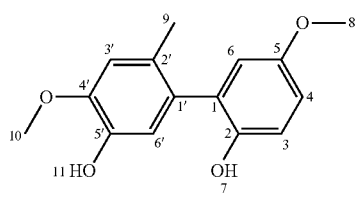

1.66 g (12 mmol, 1.0 equiv.) of 4-methylguaiacol and 4.49 g (36 mmol, 3.0 equiv.) of 4-methoxyphenol were dissolved in 80 ml of HFIP, 1.63 g of MTES were added and the electrolyte was transferred to the electrolysis cell. The solvent and unconverted amounts of reactant are removed under reduced pressure after the electrolysis, the crude product is purified by flash chromatography on silica gel 60 in a 4:1 eluent (cyclohexane:ethyl acetate) and the product is obtained as a colourless solid.

Yield: 2.05 g (66%, 7.9 mmol)
GC (hard method, HP-5): $t_R$=14.03 min
$R_f$(CH:EA=4:1)=0.33
$m_p$=118.7° C. (recrystallized from DCM/CH)
$^1$H NMR (600 MHz, DMSO) δ=2.01 (s, 3H, 9-H), 3.66 (s, 3H, 8-H), 3.77 (s, 3H, 10-H), 6.53 (d, 1H, 6-H), 6.55 (s, 1H, 6'-H), 6.72 (dd, 1H, 4-H), 6.77 (s, 1H, 3'-H), 6.79 (d, 1H, 3-H), 8.73 (s, 1H, 11-H), 8.75 (s, 1H, 7-H);
Couplings: $^3J_{3-H,4-H}$=8.7 Hz; $^4J_{4-H,6-H}$=3.0 Hz
$^{13}$C NMR (151 MHz, DMSO) δ=19.33 (C-9), 55.32 (C-8), 55.73 (C-10), 113.24 (C-4), 113.75 (C-3'), 115.99 (C-3), 116.07 (C-6), 117.40 (C-6'), 126.56 (C-2'), 129.06 (C−1), 130.95 (C-1'), 143.80 (C-5'), 146.52 (C-4'), 148.29 (C-2), 151.81 (C-5).

HRMS for $C_{15}H_{16}O_4$ (ESI+) [M+Na]$^+$: calc.: 283.0946. found: 283.0942.
MS (EI, GCMS): m/z (%): 260 (100) [M]$^+$, 245 (12) [M−CH$_3$]$^+$.
Elemental analysis for $C_{15}H_{16}O_4$: calc.: 69.22%; H, 6.20%. found: C, 69.02%; H, 6.34%.

2,2'-Dihydroxy-3-methoxy-3',5,5'-trimethylbiphenyl

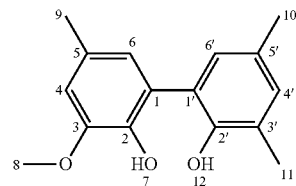

0.70 g (6 mmol, 1.0 equiv.) of 4-methylguaiacol and 2.08 g (17 mmol, 3.0 equiv.) of 2,4-dimethylphenol were dissolved in 27 ml of HFIP and 6 ml of MeOH, 0.68 g of MTES was added and the electrolyte was transferred to the electrolysis cell. The solvent and unconverted amounts of reactant are removed under reduced pressure after the electrolysis, the crude product is purified by flash chromatography on silica gel 60 in a 9:1 eluent (cyclohexane:ethyl acetate) and the product is obtained as a pale yellow solid.

Yield: 663 mg (45%, 2.5 mmol)
GC (hard method, HP-5): $t_R$=13.97 min
$R_f$(CH:EA=4:1)=0.29
$m_p$=119.7° C. (recrystallized from DCM/CH)
$^1$H NMR (400 MHz, CDCl$_3$) δ=2.34 (s, 3H, 10-H), 2.35 (s, 3H, 11-H), 2.38 (s, 3H, 9-H), 3.94 (s, 3H, 8-H), 6.16 (s, 1H, 12-H), 6.20 (s, 1H, 7-H), 6.76 (d, 1H, 4-H), 6.78 (d, 1H, 6-H), 6.98 (d, 1H, 6'-H), 7.03 (d, 1H, 4'-H);
Couplings: $^4J_{4-H,6-H}$=1.7 Hz, $^4J_{4'-H,6'-H}$=2.1 Hz;
$^{13}$C NMR (101 MHz, CDCl$_3$) δ=16.51 (C-9), 20.54 (C-10), 21.20 (C-11), 56.12 (C-8), 110.92 (C-4), 123.95 (C-6), 124.13 (C−1), 124.64 (C-1'), 126.18 (C-3'), 128.82 (C-6'), 129.59 (C-5'), 130.40 (C-5), 131.40 (C-4'), 139.46 (C-2), 146.35 (C-3), 149.42 (C-2').

HRMS for $C_{18}H_{16}O_3$ (ESI+) [M+Na]$^+$: calc.: 281.1154. found: 281.1152.
MS (EI, GCMS): m/z (%): 242 (100) [M]$^+$, 227 (38) [M−CH$_3$]$^+$.
Elemental analysis for $C_{16}H_{18}O_3$: calc.: C, 68.31%; H, 6.45%. found: C, 68.29%; H, 6.40%.

2,2'-Dihydroxy-3-methoxy-5-methyl-4'-(dimethylethyl)biphenyl

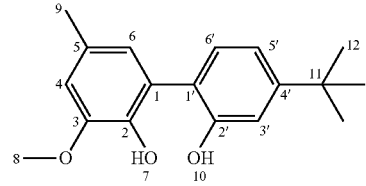

0.69 g (5 mmol, 1.0 equiv.) of 4-methylguaiacol and 2.25 g (15 mmol, 3.0 equiv.) of 3-tert-butylphenol were dissolved in 33 ml of HFIP, 0.68 g of MTES was added and the electrolyte was transferred to the electrolysis cell. The solvent and unconverted amounts of reactant are removed under reduced pressure after the electrolysis, the crude product is purified by flash chromatography on silica gel 60 in a 4:1 eluent (cyclohexane:ethyl acetate) and the product is obtained as a colourless solid.

Yield: 808 mg (63%, 3.1 mmol)
GC (hard method, HP-5): $t_R$=13.97 min
$R_f$(CH:EA=4:1)=0.29
$m_p$=160.3° C. (recrystallized from DCM/CH)
$^1$H NMR (400 MHz, CDCl$_3$) δ=1.37 (s, 9H, 12-H), 2.36 (s, 3H, 9-H), 3.94 (s, 3H, 8-H), 6.25 (s, 1H, 7-H), 6.48 (s, 1H, 10-H), 6.75 (d, 1H, 6-H), 6.79 (d, 1H, 4-H), 7.08 (dd, 1H, 5'-H), 7.12 (d, 1H, 3'-H), 7.27 (d, 1H, 6'-H);
Couplings: $^4J_{4-H,6-H}$=1.7 Hz; $^3J_{5'-H,6'-H}$=8.0 Hz, $^4J_{3'-H,5'-H}$=1.7 Hz;
$^{13}$C NMR (101 MHz, CDCl$_3$) δ=21.24 (C-9), 31.31 (C-12), 34.58 (C-11), 56.15 (C-8), 110.79 (C-4), 114.94 (C-3'), 118.30 (C-5'), 122.37 (C-1'), 123.88 (C-1), 123.94 (C-6), 130.45 (C-6'), 130.53 (C-4'), 139.24 (C-5), 146.32 (C-3), 152.91 (C-2'), 153.13 (C-2).
HRMS for C$_{15}$H$_{16}$O$_4$ (ESI+) [M+Na$^+$]: calc.: 309.1467. found: 309.1466.
MS (EI, GCMS): m/z (%): 242 (100) [M]$^+$, 227 (38) [M–CH$_3$]$^+$.
Elemental analysis for C$_{18}$H$_{22}$O$_3$: calc.: 75.50%; H, 7.74%. found: C, 75.41%; H, 7.72%.

2,2'-Dihydroxy-4',5-dimethyl-3-methoxylbiphenyl
and
2,4'-dihydroxy-2',5-dimethyl-3-methoxylbiphenyl 0.70 g (5 mmol, 1.0 equiv.) of 4-methylguaiacol and 1.65 g (15 mmol, 3.0 equiv.) of 3-methylphenol were dissolved in 33 ml of HFIP, 0.68 g of MTES was added and the electrolyte was transferred to the electrolysis cell. The solvent and unconverted amounts of reactant are removed under reduced pressure after the electrolysis, the crude product is purified by flash chromatography on silica gel 60 in a 4:1 eluent (cyclohexane:ethyl acetate) and two cross-coupling products are obtained as colourless solids.

2,2'-Dihydroxy-4',5-dimethyl-3-methoxylbiphenyl (by-product)

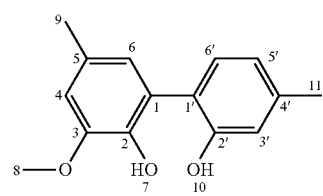

Yield: 266 mg (21%, 1.1 mmol)
GC (hard method, HP-5): $t_R$=13.72 min
$R_f$(CH:EA=4:1)=0.25
$m_p$=136.2° C. (recrystallized from DCM/CH)
$^1$H NMR (400 MHz, CDCl$_3$) δ=2.35 (s, 3H, 9-H/11-H), 2.37 (s, 3H, 9-H/11-H), 3.94 (s, 3H, 8-H), 6.17 (s, 1H, 10-H), 6.35 (s, 1H, 2-H), 6.74 (d, 1H, 4-H), 6.76 (s, 1H, 6-H), 6.88-6.83 (m, 1H, 5'-H), 6.90 (d, 1H, 3'-H), 7.21 (d, 1H, 6'-H);
Couplings: $^4J_{4-H,6-H}$=1.8 Hz, $^3J_{5'-H,6'-H}$=7.7 Hz, $^4J_{3'-H,5'-H}$=1.5 Hz;
$^{13}$C NMR (101 MHz, CDCl$_3$) δ=21.11, 21.20 (C-9/C-11), 56.13 (C-8), 110.81 (C-4), 118.25 (C-3'), 121.97 (C-5'), 122.39 (C-1), 123.77 (C-1'), 123.85 (C-6), 130.50 (C-5), 130.68 (C-6'), 139.30 (C-4'), 139.54 (C-2), 146.31 (C-3), 153.33 (C-2').
HRMS for C$_{15}$H$_{16}$O$_3$ (ESI+) [M+Na$^+$]: calc.: 267.0997. found: 267.1006.
MS (EI, GCMS): m/z (%): 244 (100) [M]$^+$, 229 (18) [M–CH$_3$]$^+$.
Elemental analysis for C$_{15}$H$_{16}$O$_3$: calc.: C, 73.75%; H, 6.60%. found: C, 73.70%; H, 6.68%.

2,4'-Dihydroxy-2',5-dimethyl-3-methoxylbiphenyl (main product)

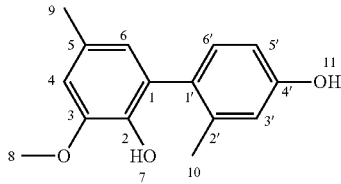 [SMILES: COc1cc(C)cc(-c2ccc(O)cc2C)c1O]

Yield: 285 mg (23%, 1.2 mmol)
GC (hard method, HP-5): $t_R$=13.81 min
$R_f$(CH:EA=4:1)=0.19
$m_p$=61.9° C. (recrystallized from DCM/CH)
$^1$H NMR (400 MHz, CDCl$_3$) δ=2.17 (s, 3H, 10-H), 2.32 (s, 3H, 9-H), 3.92 (s, 3H, 8-H), 4.77 (s, 1H, 11-H), 5.45 (s, 1H, 7-H), 6.59-6.53 (m, 1H, 6-H), 6.74-6.68 (m, 2H, 4-H/5'-H), 6.76 (d, 1H, 3'-H), 7.09 (d, 1H, 6'-H);
Couplings: $^3J_{5'-H,6'-H}$=8.2 Hz, $^4J_{3'-H,5'-H}$=2.7 Hz;
$^{13}$C NMR (101 MHz, CDCl$_3$) δ=20.04 (C-10), 21.09 (C-9), 55.97 (C-8), 110.51 (C-4), 112.53 (C-5'), 116.62 (C-3'), 123.47 (C-6), 127.28 (C-1), 128.74 (C-5), 130.02 (C-1'), 131.17 (C-6'), 138.56 (C-2'), 140.49 (C-2), 146.24 (C-3), 154.84 (C-4').
HRMS for C$_{15}$H$_{16}$O$_3$ (ESI+) [M+Na$^+$]: calc.: 267.0997. found: 267.0995.
MS (EI, GCMS): m/z (%): 244 (100) [M]$^+$, 229 (18) [M–CH$_3$]$^+$.
Elemental analysis for C$_{15}$H$_{16}$O$_3$: calc.: C, 73.75%; H, 6.60%. found: C, 73.70%; H, 6.70%.

2,2'-Dihydroxy-3-methoxy-4'-5,5'-trimethylbiphenyl

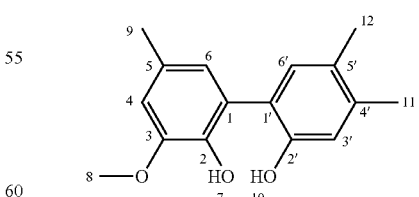

0.69 g (5 mmol, 1.0 equiv.) of 4-methylguaiacol and 1.83 g (15 mmol, 3.0 equiv.) of 3,4-dimethylphenol were dissolved in 27 ml of HFIP and 6 ml of MeOH, 0.68 g of MTES was added and the electrolyte was transferred to the electrolysis cell. The solvent and unconverted amounts of reactant are removed under reduced pressure after the electrolysis, the crude product is purified by flash chromatography on silica gel 60 in a 9:1 eluent (cyclohexane:ethyl acetate) and the product is obtained as a colourless solid.

Yield: 688 mg (52%, 2.6 mmol)

GC (hard method, HP-5): $t_R$=14.52 min $R_f$(CH:EA=4:1)=0.29

$m_p$=152.3° C. (recrystallized from DCM/CH)

$^1$H NMR (400 MHz, CDCl$_3$) δ=12.25 (s, 3H, 11-H), 2.28 (s, 3H, 12-H), 2.36 (s, 3H, 9-H), 3.93 (s, 3H, 8-H), 6.19 (s, 1H, 7-H), 6.25 (s, 1H, 10-H), 6.73 (d, 1H, 4-H), 6.76 (s, 1H, 6-H), 6.88 (s, 1H, 3'-H), 7.08 (s, 1H, 6'-H);

Couplings: $^4J_{4\text{-}H,6\text{-}H}$=1.7 Hz;

$^{13}$C NMR (101 MHz, CDCl$_3$) δ=18.89 (C-11), 19.60 (C-12), 21.24 (C-9), 56.14 (C-8), 110.74 (C-4), 118.93 (C-3'), 122.54 (C-1), 123.82 (C-6), 123.97 (C-1'), 129.03 (C-5), 130.46 (C-4'), 131.69 (C-6'), 137.94 (C-5'), 139.26 (C-2), 146.31 (C-3), 151.36 (C-2').

HRMS for C$_{16}$H$_{18}$O$_3$ (ESI+) [M+Na$^+$]: calc.: 281.1154. found: 281.1157.

MS (EI, GCMS): m/z (%): 258 (100) [M]$^+$, 243 (10) [M−CH$_3$]$^+$.

Elemental analysis for C$_{16}$H$_{18}$O$_3$: calc.: 74.39%; H, 7.02%. found: C, 74.32%; H, 7.20%.

2, 2'-Dihydroxy-5'-isopropyl-3-methoxy-5-methylbiphenyl

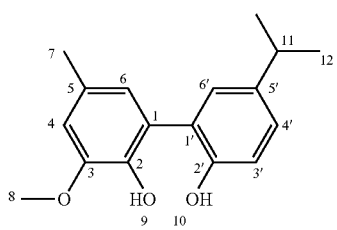 [SMILES: COc1cc(C)cc(-c2cc(C(C)C)ccc2O)c1O]

0.69 g (5 mmol, 1.0 equiv.) of 4-methylguaiacol and 2.05 g (15 mmol, 3.0 equiv.) of 4-isopropylphenol were dissolved in 27 ml of HFIP and 6 ml of MeOH, 0.68 g of MTES was added and the electrolyte was transferred to the electrolysis cell. The solvent and unconverted amounts of reactant are removed under reduced pressure after the electrolysis, the crude product is purified by flash chromatography on silica gel 60 in a 4:1 eluent (cyclohexane:ethyl acetate) and the product is obtained as a brownish oil.

Yield: 0.53 g (39%, 1.9 mmol)

GC (hard method, HP-5): $t_{R=}$14.23 min $R_f$(CH:EA=4:1)=0.30

$^1$H NMR (400 MHz, CDCl$_3$) δ=1.27 (m, 6H), 2.36 (s, 3H), 2.91 (dt, J=13.8, 6.9, 6.9 Hz, 1H), 3.94 (s, 3H), 6.13-6.27 (m, 2H), 6.82-6.65 (m, 1H), 6.25 (m, 2H), 6.75 (s, 1H), 6.77 (s, 1H), 6.99 (d, J=8.1 Hz, 1H), 7.19-7.12 (m, 2H);

$^{13}$C NMR (101 MHz, CDCl$_3$) δ=21.25, 24.27, 33.40, 56.18, 110.92, 117.60, 123.91, 124.23, 125.07, 127.29, 128.80, 130.57, 139.29, 141.42, 146.31, 151.51.

HRMS for C$_{17}$H$_{20}$O$_3$ (ESI+) [M+Na$^+$]: calc.: 295.1310. found: 295.1297.

MS (EI, GCMS): m/z (%): 272 (80) [M]$^+$, 257 (100) [M−CH$_3$]$^+$.

2,2'-Dihydroxy-3-methoxy-5-methyl-5'-tert-butylbiphenyl

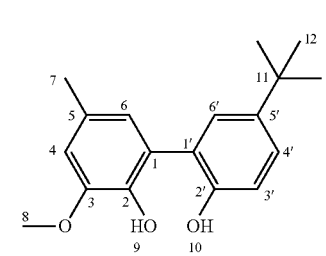 [SMILES: COc1cc(C)cc(-c2cc(C(C)(C)C)ccc2O)c1O]

0.69 g (5 mmol, 1.0 equiv.) of 4-methylguaiacol and 2.26 g (15 mmol, 3.0 equiv.) of 4-tert-butylphenol were dissolved in 27 ml of HFIP and 6 ml of MeOH, 0.68 g of MTES was added and the electrolyte was transferred to the electrolysis cell. The solvent and unconverted amounts of reactant are removed under reduced pressure after the electrolysis, the crude product is purified by flash chromatography on silica gel 60 in a 4:1 eluent (cyclohexane:ethyl acetate) and the product is obtained as a yellowish oil.

Yield: 0.48 g (34%, 1.7 mmol)

GC (hard method, HP-5): $t_R$=14.52 min $R_f$(CH:EA=4:1)=0.24

$^1$H NMR (400 MHz, CDCl$_3$) δ=1.34 (s, 9H), 2.37 (s, 3H), 3.94 (s, 3H), 6.17 (s, 1H), 6.24 (s, 1H), 6.75 (s, 1H), 6.77 (s, 1H), 6.99 (d, J=8.4 Hz, 1H), 7.31-7.29 (m, 1H), 7.33 (dd, J=8.4, 2.5 Hz, 1H).

$^{13}$C NMR (101 MHz, CDCl$_3$) δ=21.28, 31.61, 34.20, 56.18, 110.91, 117.25, 123.92, 124.41, 124.63, 126.38, 127.78, 130.58, 139.32, 143.70, 146.32, 151.22.

HRMS for C$_{18}$H$_{22}$O$_3$ (ESI+) [M+Na$^+$]: calc.: 309.1467. found: 309.1476.

MS (EI, GCMS): m/z (%): 286 (28) [M]$^+$, 271 (100) [M−CH$_3$]$^+$.

2,2'-Dihydroxy-3',5'-di-tert-butyl-5-methyl-3-methoxybiphenyl

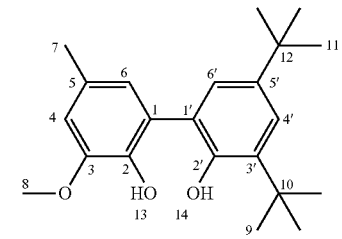 [SMILES: COc1cc(C)cc(-c2cc(C(C)(C)C)cc(C(C)(C)C)c2O)c1O]

0.69 g (5 mmol, 1.0 equiv.) of 4-methylguaiacol and 3.12 g (15 mmol, 3.0 equiv.) of 2,4-di-tert-butylphenol were dissolved in 27 ml of HFIP and 6 ml of MeOH, 0.68 g of MTES was added and the electrolyte was transferred to the electrolysis cell. The solvent and unconverted amounts of reactant are removed under reduced pressure after the electrolysis, the crude product is purified by flash chromatography on silica gel 60 in a 9:1 eluent (cyclohexane:ethyl acetate) and the product is obtained as a colourless solid.

Yield: 0.41 g (24%, 1.2 mmol)

GC (hard method, HP-5): $t_R$=15.15 min $R_f$(CH:EA=9:1)=0.35

$m_p$=120.2° C. (recrystallized in n-pentane)

$^1$H NMR (400 MHz, CDCl$_3$) δ=1.36 (s, 9H), 1.50 (s, 9H), 2.38 (s, 3H), 3.96 (s, 3H), 6.00 (s, 1H), 6.05 (s, 1H), 6.77 (s, 1H), 7.16 (d, J=2.5 Hz, 1H), 7.39 (d, J=2.5 Hz, 1H).

$^{13}$C NMR (101 MHz, CDCl$_3$) δ=21.23, 29.88, 31.69, 34.40, 35.23, 56.17, 111.03, 123.96, 124.17, 125.09, 125.50, 130.42, 136.73, 139.72, 142.36, 146.45, 149.82.

MS (EI, GCMS): m/z (%): 342 (22) [M]$^+$, 327 (100) [M−CH$_3$]$^+$.

2,2'-Dihydroxy-3',5-dimethyl-3-methoxy-5'-tert-butylbiphenyl

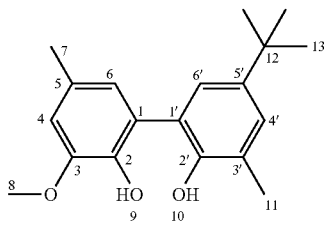 [SMILES: COc1cc(C)cc(-c2cc(C(C)(C)C)cc(C)c2O)c1O]

0.69 g (5 mmol, 1.0 equiv.) of 4-methylguaiacol and 2.47 g (15 mol, 3.0 equiv.) of 2-methyl-4-tert-butylphenol were dissolved in 27 ml of HFIP and 6 ml of MeOH, 0.68 g of MTES was added and the electrolyte was transferred to the electrolysis cell. The solvent and unconverted amounts of reactant are removed under reduced pressure after the electrolysis, the crude product is purified by flash chromatography on silica gel 60 in a 4:1 eluent (cyclohexane:ethyl acetate) and the product is obtained as a yellowish oil.

Yield: 0.69 g (46%, 2.3 mmol)

GC (hard method, HP-5): $t_R$=14.79 min $R_f$(CH:EA=4:1)=0.33

$^1$H NMR (400 MHz, CDCl$_3$) δ=1.37 (s, 9H), 2.39 (d, J=2.4 Hz, 6H), 3.94 (s, 3H), 6.15 (s, 1H), 6.17 (s, 1H), 6.77 (s, 1H), 6.79 (s, 1H), 7.17 (d, J=2.5 Hz, 1H), 7.24 (d, J=2.4 Hz, 1H);

$^{13}$C NMR (101 MHz, CDCl$_3$) δ=16.90, 21.28, 31.67, 34.12, 56.16, 110.94, 124.02, 124.17, 124.59, 125.41, 125.65, 127.86, 130.47, 139.50, 143.07, 146.40, 149.41.

MS (EI, GCMS): m/z (%): 300 (18) [M]$^+$, 285 (100) [M−CH$_3$]$^+$.

2,2'-Dihydroxy-3-methoxy-5-methyl-5'-(1-methylethyl)biphenyl

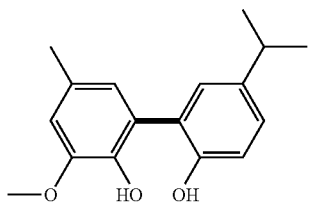

MTES was added to 0.69 g (5 mmol, 1.0 eq.) of 4-methylguaiacol and 2.05 g (15 mmol, 3.0 eq.) of 4-isopropylphenol and 0.68 g of MTES in 27 ml of HFIP+6 ml of MeOH and the electrolyte was transferred to the electrolysis cell. The solvent and unconverted amounts of reactant are removed under reduced pressure after the electrolysis, the crude product is purified by flash chromatography on silica gel 60 in a 4:1 eluent (cyclohexane:ethyl acetate) and the product is obtained as a brownish oil.

Yield: 39%, 527 mg, 1.9 mmol.

$R_f$ (cyclohexane:ethyl acetate=4:1)=0.30; $^1$H NMR (400 MHz, CDCl$_3$) δ=1.27 (m, 6H), 2.36 (s, 3H), 2.91 (sept, J=6.9 Hz, 1H), 3.94 (s, 3H), 6.13-6.27 (m, 2H), 6.65-6.82 (m, 2H), 6.99 (d, J=8.1 Hz, 1H), 7.12-7.19 (m, 2H); $^{13}$C NMR (101 MHz, CDCl$_3$) δ=21.37, 24.39, 33.53, 56.31, 111.04, 117.73, 124.04, 124.36, 125.20, 127.42, 128.93, 130.70, 139.42, 141.55, 146.44, 151.64. HRMS for C$_{17}$H$_{20}$O$_3$ (ESI+) [M+Na$^+$]: calc.: 295.1310. found: 295.1297. MS (EI, GCMS): m/z (%): 272 (80) [M]$^+$, 257 (100) [M−CH$_3$]$^+$.

2,2'-Dihydroxy-3-methoxy-5-methyl-4'-(methylethyl)biphenyl

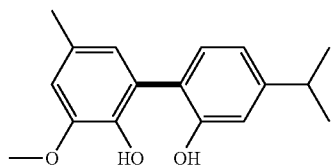

0.69 g (5 mmol, 1.0 eq.) of 4-methylguaiacol and 2.065 g (15 mmol, 3.0 eq.) of 3-isopropylphenol and 0.68 g of MTES were dissolved in 33 ml of HFIP and the electrolyte was transferred to the electrolysis cell. The solvent and unconverted amounts of reactant are removed under reduced pressure after the electrolysis, the crude product is purified by flash chromatography on silica gel 60 in a 4:1 eluent (cyclohexane:ethyl acetate) and the product is obtained as a brownish oil (yield: 52%, 705 mg, 2.6 mmol).

$R_f$ (cyclohexane:ethyl acetate=4:1)=0.29; $^1$H NMR (400 MHz, CDCl$_3$) δ=1H NMR (400 MHz, CDCl$_3$) δ 1.27 (s, 3H), 1.29 (s, 3H), 2.34 (s, 3H), 2.91 (sept, J=7.0 Hz, 1H), 3.94 (s, 3H), 6.15 (s, 1H), 6.35 (s, 1H), 6.73 (d, J=1.8 Hz, 1H), 6.75-6.77 (m, 1H), 6.90 (dd, J=7.9 Hz, 1.8 Hz, 1H), 6.94 (d, J=1.7 Hz, 1H), 7.23 (d, J=7.8 Hz, 1H). $^{13}$C NMR (101 MHz, CDCl$_3$) δ=$^{13}$C NMR (101 MHz, CDCl$_3$) δ 21.36, 24.02, 33.92, 56.30, 77.16, 110.91, 115.77, 119.56, 122.81, 124.00, 124.08, 130.65, 130.84, 139.38, 146.43, 150.72, 153.54. HRMS for C$_{17}$H$_{20}$O$_3$ (ESI+) [M+Na$^+$]: calc.: 295.1310. found: 295.1305. MS (EI, GCMS): m/z (%): 272 (100) [M]$^+$, 257 (50) [M−CH$_3$]$^+$.

Elemental anal. for C$_{17}$H$_{20}$O$_3$: calc.: 74.97%; H, 7.40%. found: C, 75.05%; H, 7.36%.

2,2'-Dihydroxy-4',5-dimethyl-3-methoxybiphenyl and 2,4'-dihydroxy-2',5-dimethyl-3-methoxybiphenyl 0.28 g (2 mmol, 1.0 eq.) of 4-methylguaiacol, 1.22 g (6 mmol, 3.0 eq.) of 3-methylphenyl and 0.77 g of MTBS were dissolved 25 ml of HFIP and the electrolyte was transferred to the beaker-type electrolysis cell. The solvent and unconverted amounts of reactant are removed under reduced pressure after the electrolysis, the crude product is purified by flash chromatography on silica gel 60 in a 4:1 eluent (cyclohexane:ethyl acetate) and led to the two cross-coupling products as a colourless and viscous oil.

2,2'-Dihydroxy-4',5-dimethyl-3-methoxylbiphenyl (by-product)

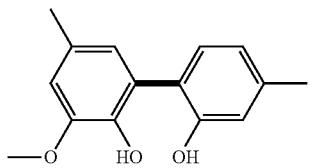

Yield: 21%, 266 mg, 1.1 mmol; $R_f$ (cyclohexane:ethyl acetate=4:1)=0.25; $m_p$=136.2° C. (crystallized from dichloromethane/cyclohexane); $^1$H NMR (400 MHz, CDCl$_3$) δ=2.35 (s, 3H), 2.37 (s, 3H), 3.94 (s, 3H), 6.17 (s, 1H), 6.35 (s, 1H), 6.74 (d, J=1.8 Hz, 1H), 6.76 (s, 1H), 6.88-6.83 (m, 1H), 6.90 (d, 1H, J=1.5 Hz), 7.21 (d, 1H, J=7.7 Hz); $^3$C NMR (101 MHz, CDCl$_3$) δ=21.11, 21.20 56.13, 110.81, 118.25, 121.97, 122.39, 123.77, 123.85, 130.50, 130.68, 139.30, 139.54, 146.31, 153.33. HRMS for C$_{15}$H$_{16}$O$_3$ (ESI+) [M+Na$^+$]: calc.: 267.0997. found: 267.1006. MS (EI, GCMS): m/z (%): 244 (100) [M], 229 (18) [M–CH$_3$]$^+$. Elemental anal. for C$_{15}$H$_{16}$O$_3$: calc.: C, 73.75%; H, 6.60%. found: C, 73.70%; H, 6.68%.

2,4'-Dihydroxy-2',5-dimethyl-3-methoxybiphenyl (main product)

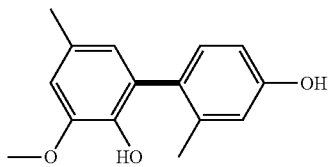

Yield: 23%, 285 mg, 1.2 mmol; $R_f$ (cyclohexane:ethyl acetate=4:1)=0.19 $m_p$=61.9° C. (crystallized from dichloromethane/cyclohexane); $^1$H NMR (400 MHz, CDCl$_3$) δ=2.17 (s, 3H), 2.32 (s, 3H), 3.92 (s, 3H), 4.77 (s, 1H), 5.45 (s, 1H), 6.59-6.53 (m, 1H), 6.74-6.68 (m, 2H), 6.76 (d, 1H, J=2.7 Hz), 7.09 (d, 1H, J=8.2 Hz); $^{13}$C NMR (101 MHz, CDCl$_3$) δ=20.04, 21.09, 55.97, 110.51, 112.53, 116.62, 123.47, 127.28, 128.74, 130.02, 131.17, 138.56, 140.49, 146.24, 154.84. HRMS for C$_{15}$H$_{16}$O$_3$ (ESI+) [M+Na$^+$]: calc.: 267.0997. found: 267.0995. MS (EI, GCMS): m/z (%): 244 (100) [M]$^+$, 229 (18) [M–CH$_3$]$^+$. Elemental anal. for C$_{15}$H$_{16}$O$_3$: calc.: C, 73.75%; H, 6.60%. found: C, 73.70%; H, 6.70%.

2,2'-Dihydroxy-5,5'-dimethyl-3'-(1,1-dimethylethyl)-3-methoxybiphenyl

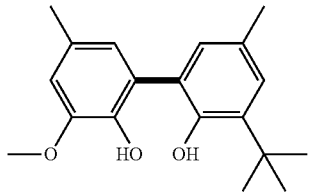

0.69 g (5 mmol, 1.0 eq.) of 4-methylguaiacol, 2.47 g (15 mmol, 3.0 eq.) of 4-methyl-2-tert-butylphenol and 0.68 g of MTES were dissolved in 27 ml of HFIP+6 ml of MeOH and the electrolyte was transferred to the electrolysis cell. The solvent and unconverted amounts of reactant are removed under reduced pressure after the electrolysis, the crude product is purified by flash chromatography on silica gel 60 in a 4:1 eluent (cyclohexane:ethyl acetate) and the product is obtained as a yellow oil (yield: 36%, 545 mg, 1.8 mmol).

$R_f$ (cyclohexane:ethyl acetate=9:1)=0.36; $^1$H NMR (400 MHz, CDCl$_3$) δ=1.46 (s, 9H), 2.34 (m, 6H), 3.93 (s, 3H), 5.99 (s, 1H), 6.01 (s, 1H), 6.74 (s, 2H), 6.96 (d, J=1.9 Hz, 1H), 7.14 (d, J=1.9 Hz, 1H); $^{13}$C NMR (101 MHz, CDCl$_3$) δ=21.05, 21.32, 29.96, 35.05, 56.30, 77.16, 111.21, 124.18, 124.24, 125.92, 127.67, 129.15, 129.22, 130.51, 137.57, 139.87, 146.57, 150.10.

HRMS for C$_{22}$H$_{30}$O$_3$ (ESI+) [M+Na$^+$]: calc.: 323.1623. found: 323.1618. MS (EI, GCMS): m/z (%): 300 (100) [M]$^+$, 285 (100) [M–CH$_3$]$^+$.

Experimental Results

Table 1 lists the yields and selectivities:

TABLE 1

| Product | Solvent | Yield (isolated)$^a$ | Selectivity (AB:BB)$^b$ |
| --- | --- | --- | --- |
| | HFIP pure | 50% | >100:1 |
| | HCOOH + 9% MeOH | 28% | >100:1 |
| | HFIP + 18% MeOH | 36% | >100:1 |
| | HCOOH + 9% MeOH | 13% | >100:1 |
| | HFIP pure | 66% | >100:1 |
| | HFIP + 18% MeOH | 45% | 9:1 |
| | HFIP pure | 21% 23% | >100:1 |

TABLE 1-continued

| Product | Solvent | Yield (isolated)[a] | Selectivity (AB:BB)[b] |
|---|---|---|---|
| 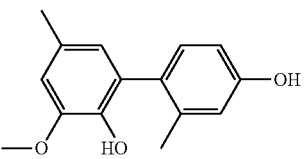 [SMILES: COc1cc(C)cc(-c2ccc(O)cc2C)c1O] | | | |
| 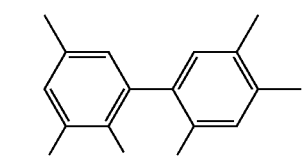 | HFIP + 18% MeOH | 52% | >100:1 |
| 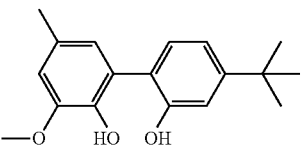 [SMILES: COc1cc(C)cc(-c2ccc(C(C)(C)C)cc2O)c1O] | HFIP pure | 63% | >100:1 |
| 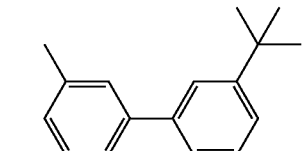 | HFIP + 18% MeOH | 34% | >100:1 |
| 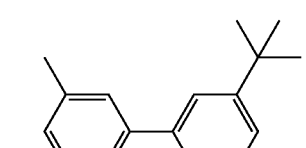 | HFIP + 18% MeOH | 24% | 4:1 |
| 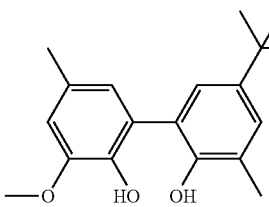 | HFIP + 18% MeOH | 46% | >100:1 |
| 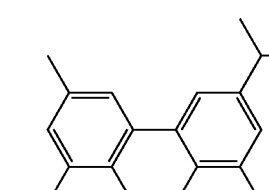 | HFIP + 18% MeOH | 39% | >100:1 |

[a] isolated yield based on n(first phenol);
[b] determined via GC. AB: cross-coupling product, BB: homo-coupling product.
HFIP: 1,1,1,3,3,3-hexafluoroisopropanol Table 1 shows that a large spectrum of structurally different phenols can be directly cross-coupled by the method described above.

Comparative Experiments

In a first experimental series (ES1) which was effected under inventive conditions, the general procedure was modified in that 0.757 mmol of the first phenol having an oxidation potential $E_{Ox}1$ and 2.271 mmol of the second phenol having an oxidation potential $E_{Ox}2$ were dissolved.

As comparative experiments, a second experimental series (ES2) was conducted. Here, the general procedure was modified in that 0.757 mmol of the first phenol having an oxidation potential $E_{Ox}1$ and 0.757 mmol of the second phenol having an oxidation potential $E_{Ox}2$ were dissolved. In the comparative experiment, the two phenols were thus present in equal portions.

TABLE 2

Comparison of yields and selectivities on reduction of the excess of one phenol component to one equivalent

| Product | ES1 selectivity[b] (AB:BB) at phenol ratio 1:3 | ES1 yield[a] at phenol ratio 1:3 | ES2 selectivity[b] (AB:BB) at phenol ratio 1:1 | ES2 yield[a] at phenol ratio 1:1 |
|---|---|---|---|---|
| 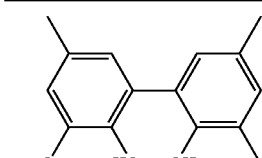 | 9:1 | 45% | 9:1 | 27% |

TABLE 2-continued

Comparison of yields and selectivities on reduction of the excess of one phenol component to one equivalent

| Product | ES1 selectivity[b] (AB:BB) at phenol ratio 1:3 | ES1 yield[a] at phenol ratio 1:3 | ES2 selectivity[b] (AB:BB) at phenol ratio 1:1 | ES2 yield[a] at phenol ratio 1:1 |
|---|---|---|---|---|
| 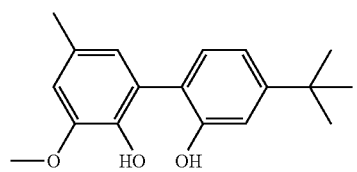 | >100:1 | 63% | 5:1 | 42% |

Electrolysis parameters: n(phenol1) = 0.757 mmol, conductive salt: MTES, c(MTES) = 0.09M, V(solvent) = 5 ml, anode: BDD/Si, cathode: BDD/Si, j = 2.8 mA/cm², T = 50° C., Q = 2 F*n(phenol1). The electrolysis is effected under galvanostatic conditions.
[a]isolated yield based on n(phenol1);
[b]determined via GC. AB: cross-coupling product, BB: homo-coupling product.

It can be clearly inferred from Table 2 that, under non-inventive conditions, i.e. in the second experimental series (ES2), much poorer yields are achieved than in the first experimental series (ES1) under inventive experimental conditions.

Influence of the Solvent

TABLE 3

Influence of the MeOH addition on the oxidation potential

| Substrate | 5.2% MeOH | 7.9% MeOH | 10.6% MeOH | 13.4% MeOH | 16.3% MeOH | 19.2% MeOH | 22.1% MeOH | 25.1% MeOH |
|---|---|---|---|---|---|---|---|---|
| 1st phenol | 0.687 | 0.675 | 0.664 | 0.660 | 0.655 | 0.653 | 0.651 | 0.653 |
| 2nd phenol | 0.823 | 0.818 | 0.820 | 0.821 | 0.824 | 0.842 | 0.849 | 0.865 |
| ΔE [V] | 0.136 | 0.143 | 0.156 | 0.161 | 0.169 | 0.189 | 0.198 | 0.212 |

1st phenol:

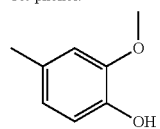

2nd phenol:

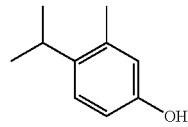

The oxidation potential of each of the two phenols shown was determined in a measurement series. The determination was effected here in 1,1,1,3,3,3-hexafluoroisopropanol (HFIP) and methanol (MeOH), with variation in the amount of methanol (MeOH) (the figures are % by volume).

Working electrode: glassy carbon, counterelectrode: glassy carbon,
Reference electrode: Ag/AgCl, v=10 mV/s,
Oxidation criterion: I=0.1 mA/cm², c(phenol)=0.152 M,
Conductive salt: MTES, c(MTES)=0.09 M.
Solvents: HFIP and MeOH The experimental series show clearly that the addition of methanol can noticeably increase the difference in the two oxidation potentials (ΔE).

Influence of the oxidation potential differences ($\Delta E_{Ox}$) on yields and selectivities Cyclic voltammetry measurements on substrates used show that differences between individual oxidation potential differences ($\Delta E_{Ox}$) correlate with selectivities and yields of the electrochemical cross-coupling phenols. A greater potential difference results in better yields and improved selectivities.

TABLE 4

$\Delta E_{Ox}$ as a function of the para substituents

| Solvent mixture | HFIP pure | 18% MeOH |
|---|---|---|
| Coupling partner | 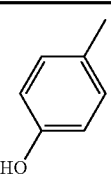 | |
| ΔE with 4-methylguaiacol | GC: 5% + 3% BP<br>Δ = −0.31 V | GC: 14%<br>Δ = −0.32 V |

TABLE 4-continued

ΔE$_{Ox}$ as a function of the para substituents

| Solvent mixture | HFIP pure | 18% MeOH |
|---|---|---|
| Coupling partner | 4-tert-butylphenol | |
| ΔE with 4-methylguaiacol | GC: 9% + 1% BP<br>Δ = −0.22 V | GC: 10%<br>Δ = −0.26 V |
| Coupling partner | 4-methoxyphenol | |
| ΔE$_{Ox}$ with 4-methylguaiacol | GC: 23%<br>Δ = −0.13 V | GC: 2%<br>Δ = −0.05 V |

Working electrode: glassy carbon, counterelectrode: glassy carbon, reference electrode: Ag/AgCl in sat. LiCl/EtOH, v = 10 mV/s, oxidation criterion: I = 0.05 mA/cm$^2$, c(phenol) = 0.152M, conductive salt: MTES, c(MTES) = 0.09M. Solvent: HFIP. ΔE$_{Ox}$ = E(ox.pot.$_{coupling\ partner}$-ox.pot.$_{table\ entry}$). BP: by-product; GC: gas chromatography integration of product ratios.

In FIG. 3, the dependence of the oxidation potential ΔE$_{Ox}$ of the para substituents on the amount of methanol added is plotted. With rising methanol concentration in HFIP, lowering of the oxidation potentials (E$_{Ox}$) of almost all para-substituted phenols is apparent. Only the isopropyl derivative beyond 15% shows a slight rise by about 50 mV.

Table 4 shows that the greatest possible ΔE$_{Ox}$ are advantageous here. Entry 1 shows a ΔE$_{Ox}$ greater by 10 mV in the HFIP/MeOH system than in pure HFIP, which results in an excellent selectivity for formation of the cross-coupling product. By-products such as homo-coupling products are also the consequence in Entry 2: here, ΔE$_{Ox}$=−0.22 V appears to be much too small to avoid homo-coupling. Side reactions can also severely reduce the yield, as shown by Entry 3. Here, a ΔE$_{Ox}$ in HFIP/MeOH of only −0.05 V causes a collapse in the amount of cross-coupling product formed.

TABLE 5

ΔE$_{Ox}$ as a function of the meta substituents

| Solvent mixture | HFIP pure | 18% MeOH |
|---|---|---|
| Coupling partner | 3-isopropylphenol | |
| ΔE$_{Ox}$ with 4-methylguaiacol | GC: 8% + 6% BP<br>Δ = −0.14 V | GC: 8% + 2% BP<br>Δ = −0.41 V |
| Coupling partner | 3-tert-butylphenol | |
| ΔE$_{Ox}$ with 4-methylguaiacol | GC: 16%<br>Δ = −0.13 V | GC: 11%<br>Δ = −0.25 V |
| Coupling partner | 3-methoxyphenol | |
| ΔE$_{Ox}$ with 4-methylguaiacol | GC: 4%<br>Δ = 0.16 V | GC: 0%<br>Δ = −0.13 V |

Working electrode: glassy carbon, counterelectrode: glassy carbon, reference electrode: Ag/AgCl in sat. LiCl/EtOH, v = 10 mV/s, oxidation criterion: I = 0.05 mA/cm$^2$, c(phenol) = 0.152M, conductive salt: MTES, c(MTES) = 0.09M. Solvent: HFIP. ΔE$_{Ox}$ = ox.pot.$_{coupling\ partner}$-ox.pot.$_{table\ entry}$. BP: by-product; gas chromatography integration of product ratios.

In FIG. 4, the dependence of the oxidation potential ΔE$_{Ox}$ of the meta substituents on the amount of methanol added is plotted. For the corresponding meta-substituted derivatives, the behaviour is similar for 3-methyl- and 3-methoxyphenol. In the case of larger radicals such as isopropyl and tert-butyl, the profile of E$_{Ox}$ is more complex. In these cases, there is a gradual increase of E$_{Ox}$ from about 13% v/v MeOH.

Table 5 shows, in Entry 1, that the optimal ΔE$_{Ox}$ window has not been found, either in pure HFIP or with an 18% MeOH content. In both cases, by-products occur, and the GC product integrals suggest only relatively small amounts of the cross-coupling product. Entry 2 shows, with a rising ΔE$_{Ox}$ (here |ΔE|=0.25 V), a loss in yield. The optimum here appears to be at 0.13 V<|ΔE$_{optimal}$|<0.25 V. The limit of |ΔE|=0.13 V is confirmed in Entry 3. No cross-coupling product formation occurs here, whereas, with slightly greater ΔE$_{Ox}$ in pure HFIP, traces of the desired biphenol are isolable here.

TABLE 6

ΔE$_{Ox}$ of further phenol substitution patterns

| Solvent mixture | HFIP pure | 18% MeOH |
|---|---|---|
| Coupling partner | 2-methyl-4-isopropylphenol | |
| ΔE$_{Ox}$ with 4-methylguaiacol | GC: 15%<br>Δ = 0.19 V | GC: 10%<br>Δ = 0.07 V |

Working electrode: glassy carbon, counterelectrode: glassy carbon, reference electrode: Ag/AgCl in sat. LiCl/EtOH, v = 10 mV/s, oxidation criterion: I = 0.05 mA/cm$^2$, c(phenol) = 0.152M, conductive salt: MTES, c(MTES) = 0.09M. Solvent: HFIP. ΔE$_{Ox}$ = ox.pot.$_{coupling\ partner}$-ox.pot.$_{table\ entry}$. BP: by-product; gas chromatography integration of product ratios.

Table 6 reflects the dependence on the respective substrate classes of the $\Delta E_{Ox}$ window sizes. The importance of the size of $\Delta E_{Ox}$ on the selectivity of the reaction is confirmed thereby.

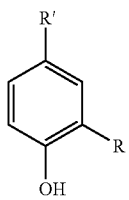

TABLE 7

$\Delta E_{Ox}$ of 2,4-disubstituted phenols
In FIG. 5, the dependence of the oxidation potential $\Delta E_{Ox}$ of the 2,4-disubstituted phenols on the amount of methanol added is plotted. 2,4-Disubstituted phenols show, within the margin of error, a distinct drop in the oxidation potential with increasing methanol concentration.

| Coupling partner | HFIP pure | 18% MeOH |
|---|---|---|
| $\Delta E_{Ox}$ with 4-methylguaiacol | GC: 10% + 4% BP $\Delta$ = 0.01 V | 23% + 4% BP $\Delta$ = -0.03 V |
| $\Delta E_{Ox}$ with 4-methylguaiacol | GC: 3% + 1% BP $\Delta$ = -0.01 V | 11% + 2% BP $\Delta$ = -0.02 V |
| $\Delta E_{Ox}$ with 4-methylguaiacol | GC: 0% $\Delta$ = 0.06 V | GC: 0% $\Delta$ = 0.08 V |

Working electrode: glassy carbon, counterelectrode: glassy carbon, reference electrode: Ag/AgCl in sat. LiCl/EtOH, v = 10 mV/s, oxidation criterion: I = 0.05 mA/cm², c(phenol) = 0.152M, conductive salt: MTES, c(MTES) = 0.09M. Solvent: HFIP. $\Delta E_{Ox}$ = ox.pot.-$_{coupling\ partner}$-ox.pot.$_{table\ entry}$. BP: by-product; gas chromatography integration of product ratios.

Table 7 reflects the complexity of the $\Delta E_{Ox}$ window sizes. According to the substitution pattern, even small $\Delta E_{Ox}$ (Entry 2, here $\Delta E_{Ox}$=-20 mV) already cause distinct selectivity for product formation. Generally, the importance of the size of $\Delta E_{Ox}$ for the selectivity of the reaction is confirmed. Entry 1, for the coupling with 2,3-dimethylphenol, shows a high proportion of homo-coupling products in pure HFIP. This can be explained by the virtually identical oxidation potential of the two co-reactants. Only in the case of MeOH addition does a $\Delta E_{Ox}$ of -30 mV develop. Only then is the formation of the unsymmetric product actually possible. If there is a fall in the difference in the oxidation potentials of phenols used, product formation is suppressed (Entry 2, pure HFIP). In the case of 3-(1,1-dimethylethyl)-4-methoxyphenol (Entry 3), this is entirely absent, since the latter phenol derivative is oxidized first and cross-coupling is impossible.

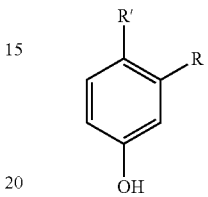

TABLE 8

$\Delta E_{Ox}$ of 3,4-disubstituted phenols
In FIG. 6, the dependence of the oxidation potential $\Delta E_{Ox}$ of the 3,4-disubstituted phenols on the amount of methanol added is plotted. Apart from 3,4-dimethylphenol, a slight lowering of $E_{ox}$ for all phenols is observed here too. More electron-deficient derivatives experience virtually constant lowering in potential from about 18% v/v methanol.

| Coupling partner | HFIP pure | 18% MeOH |
|---|---|---|
| $\Delta E_{Ox}$ with 4-methylguaiacol | GC: 11% $\Delta$ = -0.33 V | GC: 18% $\Delta$ = -0.17 V |

Working electrode: glassy carbon, counterelectrode: glassy carbon, reference electrode: Ag/AgCl in sat. LiCl/EtOH, v = 10 mV/s, oxidation criterion: j = 0.10 mA/cm², c(phenol) = 0.152M, conductive salt: MTES, c(MTES) = 0.09M. Solvent: HFIP. $\Delta E_{Ox}$ = ox.pot.-$_{coupling\ partner}$-ox.pot.$_{table\ entry}$. BP: by-product; gas chromatography integration of product ratios If the difference between the two potentials becomes too great (Table 8, $\Delta E_{Ox}$=-330 mV, HFIP pure), there is apparently electrochemical combustion of the 4-methylguaiacol used.

By the experiments conducted, it has been shown that the difference between the oxidation potentials ($\Delta E$) of the two phenols can be influenced via the solvent or solvent mixtures. In addition, it has been shown that the difference between the oxidation potentials ($\Delta E$) of the two phenols has a distinct effect on the coupling behaviour/outcome. It has thus been demonstrated that the coupling reaction of two phenols having different oxidation potentials can be controlled via the appropriate choice of solvent or solvent mixture.

The invention claimed is:
1. An electrochemical process for preparing a biphenol, the electrochemical process comprising:
preparing a reaction solution by introducing a solvent or solvent mixture, a conductive salt, a first phenol having an oxidation potential $|E_{Ox}1|$, a second phenol having an oxidation potential $|E_{Ox}2|$ into a reaction vessel, where: $|E_{Ox}2|>|E_{Ox}1|$ and $|E_{Ox}2|-|E_{Ox}1|=|\Delta E|$, the sec- ond phenol being added in excess relative to the first phenol, and the solvent or solvent mixture being selected such that |ΔE| ranges from 10 mV to 450 mV, wherein the reaction solution is free of a fluorinated compound and transition metals, introducing two electrodes into the reaction solution, applying a voltage to the electrodes, and coupling the first phenol to the second phenol to produce the biphenol.

2. The electrochemical process according to claim 1, wherein the second phenol is used at least in twice the amount relative to the first phenol.

3. The electrochemical process according to claim 1, wherein a ratio of the first phenol to the second phenol ranges from 1:2 to 1:4.

4. The electrochemical process according to claim 1, wherein either the first phenol or the second phenol has an —O-alkyl group.

5. The electrochemical process according to claim 1, wherein the solvent or solvent mixture is selected such that |ΔE| ranges from 20 mV to 400 mV.

6. The electrochemical process according to claim 1, wherein the reaction solution does not comprise an organic oxidizing agent.

7. The electrochemical process according to claim 1, wherein the first phenol and the second phenol are selected from the group consisting of Ia, Ib, IIa, IIb, IIIa and IIIb:

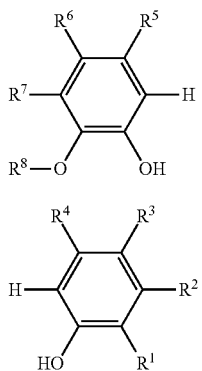

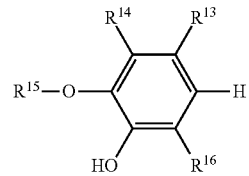

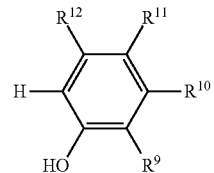

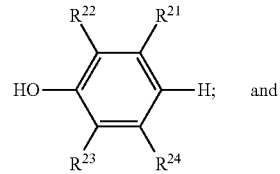

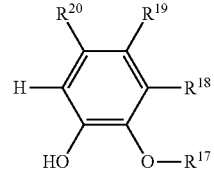

where $R^2$, $R^3$, $R^4$, $R^5$, $R^6$, $R^7$, $R^{10}$, $R^{11}$, $R^{12}$, $R^{13}$, $R^{14}$, $R^{16}$, $R^{18}$, $R^{19}$, $R^{20}$, $R^{21}$ and $R^{24}$ are selected from the group consisting of —H, -alkyl and —O-alkyl;

$R^8$, $R^{15}$ and $R^{17}$ are -alkyl;

$R^1$, $R^9$, $R^{22}$ and $R^{23}$ are selected from the group consisting of —H and -alkyl, and the first phenol is combined with the second phenol as follows:
the first phenol is Ia and the second phenol is Ib;
the first phenol is Ib and the second phenol is Ia;
the first phenol is IIa and the second phenol is IIb;
the first phenol is IIb and the second phenol is IIa;
the first phenol is IIIa and the second phenol is IIIb;
the first phenol is IIIb and the second phenol is IIIa.

8. The electrochemical process according to claim 7, wherein either the first phenol or the second phenol is Ib, and $R^1$ and $R^2$ are not both —H with the proviso that $R^3$ is methyl.

* * * * *